United States Patent [19]
Roemmele et al.

[11] Patent Number: 6,087,535
[45] Date of Patent: Jul. 11, 2000

[54] PROCESS FOR CHLOROALKYNES AND ALKYNYL AMINES

[75] Inventors: Renee Caroline Roemmele, Maple Glen; Andrew William Gross, Hatboro; David Wayne Mosley, Horsham, all of Pa.

[73] Assignee: Rohm and Haas Company, Phila, Pa.

[21] Appl. No.: 09/226,825

[22] Filed: Jan. 7, 1999

Related U.S. Application Data

[60] Provisional application No. 60/078,123, Mar. 16, 1998.

[51] Int. Cl.[7] .................................................. C07C 209/00
[52] U.S. Cl. ......................... 564/484; 564/485; 570/189; 570/217
[58] Field of Search .................................. 564/484, 485; 570/189, 217

[56] References Cited

U.S. PATENT DOCUMENTS 2,766,285 10/1956 Hennion et al. .
5,254,584 10/1993 Michelotti et al. .

FOREIGN PATENT DOCUMENTS 50-121207 9/1975 Japan .

OTHER PUBLICATIONS

Stammann, et al., Umsetzung von 3–Chlor–3–methyl–1–butin mit Chlorwasserstoff: Hinweise gegen eine elektrophile Additionsreaktion, Chemische Berichte, vol. 113, 3103–3111 (1980) (No translation).

Hennion, et al., Sterically Crowded Amines. IV. Secondary and Tertiary Bispropargylic Amines and Their Hydrogenation Products, J. Org. Chem., vol. 30, 2645–2650 (1965) month unavailable.

Hennion, et al., The Preparation of Some Acetylenic Primary Amines, J. Am. Chem. Soc., 75, 1653 (1953).

Hennion, et al., Preparation of t–Acetylenic Chlorides, J. Org. Chem., 26, 725 (1961).

Kopka, et al., Preparation of a Series of Highly Hindered Secondary Amines, Including Bis(triethylcarbinyl)amine, J. Org. Chem., 45, 4616 (1980).

*Primary Examiner*—Samuel Barts
*Attorney, Agent, or Firm*—Clark R. Carpenter

[57] ABSTRACT

This invention provides an improved process for the preparation of chloroalkynes from alkynyl alcohols. The chloroalkynes can be employed to prepare alkynyl amines which are useful for the manufacture of biologically active materials. The present invention reduces the hazards of the chlorination reaction, eliminates or greatly reduces by-product formation, and provides certain environmental benefits.

13 Claims, No Drawings

PROCESS FOR CHLOROALKYNES AND ALKYNYL AMINES

This application claims benefit of Provisional application Ser. No. 60/078,123 filed Mar. 16, 1998.

This invention relates to an improved process for the preparation of tertiary chloroalkynes from tertiary alkynyl alcohols. The tertiary chloroalkynes can be employed to prepare tertiary alkynyl amines which are useful for the manufacture of biologically active materials.

Current methods of making chloroalkynes involve the use of high excesses of hydrogen chloride at low temperature and give only moderate yields of desired product with the concomitant formation of multiple by-products. Current methods of alkynyl amine preparation involve the use of either high pressure or aqueous ammonia. The former is inconvenient and expensive while the latter results in the formation of a significant amount of alcohol by-product. The methods of this invention thus result in a more economically viable process and the ability to offer the subsequent pesticidal product to the marketplace in a more economical fashion.

The present invention substitutes excess calcium chloride in aqueous hydrochloric acid for the fuming hydrochloric acid or thionyl chloride solutions currently in use for chloroalkyne formation from alkynyl alcohols. This reduces the hazards of the reaction as well as either eliminating or greatly reducing by-product formation. Furthermore, the process of the present invention does not require any use of a copper bronze powder as a catalyst and allows greatly reduced amounts of copper(I) chloride compared to previous teachings. The reduced levels of copper eliminate the need for recycling that material or of disposing of it in the environment. For the conversion of the chloroalkyne to the alkynyl amine, anhydrous ammonia or an amine is used at either low temperature or moderate pressure in the presence of caustic to give the product in high yield and without formation of alcohol by-product.

Processes for the formation of chloroalkynes from alkynyl alcohols have been described by Kopka et al. in *J. Org. Chem.*, 45, 4616 (1980) and Hennion et al. in *J. Org. Chem.* 26, 725 (1961). Processes for the amination of chloroalkynes have been described by Michelotti et al. in U.S. Pat. No. 5,254,584, Hennion et al. in *J. Am. Chem. Soc.*, 75, 1653 (1953), Kopka et al. in *J. Org. Chem.*, 45, 4616 (1980) and Yokoyama et al. in Japanese Kokai Patent SHO 50-121207. However, none of these disclosures provide the overall advantages of economic and environmental desirability that are offered by the processes of this invention.

In one embodiment of this invention, there is provided a process for preparing a chloroalkyne that comprises reacting an alkynyl alcohol with concentrated hydrochloric acid in the presence of anhydrous calcium chloride or calcium dichloride dihydrate and a copper catalyst to produce a chloroalkyne.

More specifically, this embodiment provides a process for preparing a chloroalkyne that comprises reacting an alkynyl alcohol having the formula

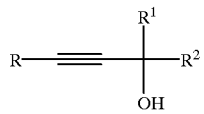

with from about 0.5 to about 10 equivalents of concentrated hydrochloric acid in the presence of from about 0.25 to about 4 equivalents of anhydrous calcium chloride or calcium dichloride dihydrate and from about 0.001 to about 0.5 equivalent of a copper catalyst to produce a chloroalkyne having the formula

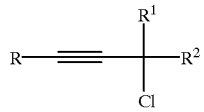

wherein

R is a hydrogen atom, alkyl, cycloalkyl, cycloalkylalkyl or aralkyl and $R^1$ and $R^2$ are each independently alkyl, cycloalkyl, cycloalkylalkyl, aralkyl or, together with the carbon atom to which they-are attached, form cycloalkyl.

In a preferred embodiment of this invention, R is a hydrogen atom or lower alkyl, $R^1$ and $R^2$ are each independently lower alkyl or, together with the carbon atom to which they are attached, form cyclopentyl or cyclohexyl. From about 2 to about 4 equivalents of concentrated hydrochloric acid are employed in the presence of from about 0.5 to about 2 equivalents of anhydrous calcium chloride or calcium dichloride dihydrate and from about 0.005 to about 0.1 equivalent of the copper catalyst. The copper catalyst is a copper(I) salt or copper powder in this preferred embodiment.

In a more preferred embodiment of this invention, R is a hydrogen atom, $R^1$ and $R^2$ are independently methyl or ethyl, and the copper catalyst is a copper(I) halide or copper(I) oxide. From about 0.75 to about 1.5 equivalents of calcium chloride dihydrate and from about 0.01 to about 0.075 equivalent of the copper(I) halide or copper(I) oxide are employed in this more preferred embodiment.

In an even more preferred embodiment of this invention, $R^1$ is methyl, $R^2$ is methyl or ethyl, and the copper catalyst is about 0.05 equivalent of copper(I) chloride.

In the above embodiment of this invention, a suitable reaction temperature is from about −20° C. to about 50° C., preferably from about −5° C. to about 30° C.

In a second embodiment of this invention, there is provided a process for preparing an alkynyl amine that comprises reacting alkynyl alcohol with concentrated hydrochloric acid in the presence of anhydrous calcium chloride or calcium dichloride dihydrate and a copper catalyst to produce a chloroalkyne in a first step followed by an optional distillation of the chloroalkyne to a purity ≧98%, and then reacting the chloroalkyne with anhydrous ammonia or an amine in the presence of a strong base in a second step.

More specifically, this embodiment provides a process for preparing an alkynyl amine that comprises (i) reacting an alkynyl alcohol having the formula

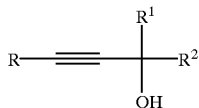

with from about 0.5 to about 10 equivalents of concentrated hydrochloric acid in the presence of from about 0.25 to about 4 equivalents of anhydrous calcium chloride or calcium dichloride dihydrate and from about 0.001 to about 0.5 equivalent of a copper catalyst to produce a chloroalkyne having the formula

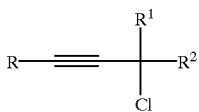

followed by an optional distillation of the chloroalkyne to a purity ≧98%, and (ii) reacting the chloroalkyne with from about 1 to about 20 volume equivalents of anhydrous ammonia or an amine having the formula $HNR^3R^4$ in the presence of from about 1.0 to about 1.5 equivalents of a strong base selected from the group consisting of sodium hydroxide, potassium hydroxide, lithium amide and sodium amide to produce the alkynyl amine having the formula

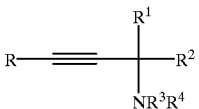

wherein

R is a hydrogen atom, alkyl, cycloalkyl, cycloalkylalkyl or aralkyl, $R^1$ and $R^2$ are each independently alkyl, cycloalkyl, cycloalkylalkyl, aralkyl or, together with the carbon atom to which they are attached, form cycloalkyl, and $R^3$ and $R^4$ are each independently a hydrogen atom, lower alkyl or, together with the nitrogen atom to which they are attached, form pyrrolidinyl or piperidinyl.

In a preferred mode of the second embodiment of this invention, R is a hydrogen atom or lower alkyl, $R^1$ and $R^2$ are each independently lower alkyl or, together with the carbon atom to which they are attached, form cyclopentyl or cyclohexyl, and $R^3$ and $R^4$ are each independently a hydrogen atom or lower alkyl. From about 2 to about 4 equivalents of concentrated hydrochloric acid are employed in the presence of from about 0.5 to about 2 equivalents of anhydrous calcium chloride or calcium dichloride dihydrate and from about 0.005 to about 0.1 equivalent of the copper catalyst. In this first step, the copper catalyst is a copper(I) salt or copper powder in this preferred mode of the second embodiment. Furthermore, a distillation of the resulting chloroalkyne to a purity ≧98% is desirable using a temperature of from about 35° C. to about 140° C. and a pressure of from about 2.6 kPa to about 102 kPa. In the second step of this preferred mode of the second embodiment, from about 1.0 to about 1.25 equivalents of sodium hydroxide, potassium hydroxide or lithium amide are used in the presence of from about 1 to about 10 volume equivalents of anhydrous ammonia or amine.

In a more preferred mode of the second embodiment of this invention, R is a hydrogen atom, $R^1$ and $R^2$ are each independently methyl or ethyl, and the copper catalyst is a copper(I) halide or copper(I) oxide. From about 0.75 to about 1.5 equivalents of calcium chloride dihydrate and from about 0.01 to about 0.075 equivalent of the copper(I) halide or copper(I) oxide are employed in the first step of the more preferred mode of the second embodiment. The distillation of the chloroalkyne is carried out using a temperature of from about 40° C. to about 80° C. and a pressure of from about 2.6 kPa to about 27 kPa. In the second step of this more preferred mode of the second embodiment, $R^3$ and $R^4$ are both hydrogen atoms and about 1.05 equivalents of sodium hydroxide are used in the presence of from about 1 to about 6 volume equivalents of anhydrous ammonia.

In an even more preferred mode of the second embodiment of this invention, $R^1$ is methyl, $R^2$ is methyl or ethyl, and the copper catalyst is about 0.05 equivalent of copper(I) chloride. The distillation of the chloroalkyne is carried out using a temperature of from about 45° C. to about 75° 0C. and a pressure of from about 7.5 kPa to about 21 kPa.

In the above second embodiment of this invention, a suitable reaction temperature is from about –20° C. to about 50° C., preferably from about 0° C. to about 30° C., in the first step. In the second step, the reaction is suitably conducted at a temperature of from about –33° C. to about 50° C. at a pressure of from about 2.6 kPa to about 102 kPa, preferably from about –33° C. to about 10° C. at a pressure of from about 2.6 kPa to about 27 kPa.

In this invention, alkyl is straight or branched chain ($C_1$–$C_8$)alkyl and includes, for example, methyl, ethyl, n-propyl, isopropyl, n-butyl, isobutyl, sec-butyl, tert-butyl, n-amyl, isoamyl, n-hexyl and n-octyl. Lower alkyl is straight or branched chain ($C_1$–$C_4$)alkyl.

Cycloalkyl includes, for example, cyclopentyl and cyclohexyl.

Cycloalkylalkyl includes, for example, cyclopentylmethyl, cyclohexylethyl, 3-cyclopentylpropyl, 4-cyclohexylbutyl and the like.

For aralkyl, the aryl part of the moiety is defined as phenyl or phenyl substituted with one or two substituents independently selected from halo and alkyl; the alkyl part of the moiety is defined as straight chain ($C_1$–$C_4$)alkyl. Examples of aralkyl include benzyl, phenethyl, 4-chlorobenzyl, 4-methylbenzyl and 2-chlorophenethyl.

A volume equivalent is defined as being equal to an identical quantity by volume. As an example, if 15 mL of chloroalkyne is present, 1 volume equivalent of anhydrous ammonia would be 15 mL; 2 volume equivalents would be 30 mL, etc.

The reaction of the first embodiment is conveniently carried out by adding the copper catalyst to a concentrated solution of aqueous hydrochloric acid (about 37% HCl). More dilute solutions of hydrochloric acid reduce the yield and purity of the desired chloroalkynes. The resulting reaction mixture is cooled to the desired reaction temperature and the calcium chloride, either anhydrous or the dihydrate, is added. While mixing, the alkynyl alcohol is added over a convenient timeframe and the mixture is stirred until the alcohol is converted to the chloroalkyne.

Step 1 of the second embodiment is carried out as described for the first embodiment. Most usually, the chloroalkyne is purified by distillation as described hereinbefore prior to Step 2. In Step 2, the chloroalkyne is added to the anhydrous ammonia in a liquid state followed by the addition of the strong base. However, addition of the chloroalkyne to a solution of the strong base and ammonia is difficult because the solution solidifies. The reaction mixture is warmed and the ammonia is allowed to evaporate. Sufficient water is added to the reaction to just dissolve the sodium chloride by-product that has formed. In the most simple product work-up option, the layers are separated and the organic phase is the alkynyl amine product. However, when the alkynyl amine is to be further purified by distillation, it is more preferable to extract the alkynyl amine after the water has been added to dissolve the sodium chloride by-product. Suitable extractants include, but are not limited to, aliphatic ($C_5$–$C_8$)hydrocarbons such as a pentane, a hexane or a heptane, aromatic hydrocarbons such as benzene or toluene, aliphatic hydrocarbons substituted with one or more chloro such as dichloromethane, and chlorobenzene. This extraction procedure results in higher yield of desired alkynyl amine. Furthermore, the subsequent distillative procedure to produce the alkynyl amine in very high purity is greatly simplified since a water azeotrope at about 88–90° C. containing a number of impurities besides the desired product is circumvented.

The following compounds in Table I are meant to further illustrate the present invention and are not limiting to its scope which is defined by the claims. The chloroalkynes listed in Table 1 were made using the following procedures in Examples 1 and 2.

EXAMPLE 1

Procedure Used to Synthesize Chloroalkynes from Alkynyl Alcohols

To 375 mL (449 g, 4.56 mol) of concentrated hydrochloric acid in a one liter resin kettle equipped with an addition funnel, thermocouple, a stirrer and external cooling jacket was added 7.52 g (76 mmol) of copper(I) chloride. The reaction was cooled to 10° C. at which time 168 g (1.14 mol) of calcium chloride dihydrate was added and cooling continued to 0° C. The alkynyl alcohol (1.52 mol) was added over three hours via a dip tube and stirring was continued for an additional hour. The reaction was warmed to 15° C., the layers were separated, the organic was washed with water and saturated sodium bicarbonate before drying with saturated sodium chloride to give the chloroalkyne product in the yield and purity shown in Table I. Products were identified by comparison to authentic standards.

EXAMPLE 2

Procedure Used to Synthesize Alkynyl Amines from Chloroalkynes

To approximately 40 mL of anhydrous ammonia at -33° C. was added 100 mmol of chloroalkyne followed by the dropwise addition of 105 mmol of 50 wt % sodium hydroxide over five minutes. The reaction was warmed to room temperature and the ammonia was allowed to evaporate. Sufficient water was added to the reaction to just dissolve the sodium chloride that had formed. The layers were separated and the organic phase was the alkynyl amine product in the yields and purities shown in Table I. Products were identified by comparison to authentic standards.

EXAMPLE 3

Procedure Used to Purify Chloroalkynes by Distillation

A total of 342 g of crude chloroalkyne with a purity of 84% was charged to a 500 mL 3-neck roundbottom flask equipped with a thermometer, a five tray one inch Oldershaw column attached to a condenser equipped with a reflux splitter. The system was evacuated and the pressure slowly reduced to 16 kPa. The pot temperature was raised to 55° C. and, after reflux was established, the split ratio was set to 3:1 and a first fraction was collected with a heard temperature of 40–48° C. The pressure was then slowly reduced to 12.7 kPa as the product was collected with a head temperature of 45° C. A total of 240 g of 97% product was collected representing an 85% recovery of chloroalkyne. A subsequent run yielded a 90% recovery of chloroalkyne.

EXAMPLE 4

Procedure Used to Purify Alkynyl Amines by Distillation

After adding water to dissolve sodium chloride as in Example 2, the system is extracted with hexanes (0.56 mL hexanes/g of crude chloride) and the layers separated. The aqueous was extracted once more with two thirds the original volume of hexanes before separating the layers and combining the hexanes extracts. The hexanes solution of product was then azeotropically dried using a Dean Stark trap. Product distillation is carried out at atmospheric pressure using a 10 tray one inch vacuum jacketed Older-Shaw column. Hexanes were removed up to 80° C. and a forecut taken from 80–103° C. The product (Compound 2) was taken off from 104–106° C. in an overall yield from starting alcohol, using crude chloride, of 75% and a purity of 99.3%.

It should be understood that the instant specification is set forth by way of illustration and not limitation, and that various modifications and changes can be made without departing from the spirit and scope of the present invention as defined by the appended claims.

We claim:

1. A process for preparing a chloroalkyne that consists of reacting an alkynyl alcohol having the formula

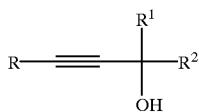

with from about 0.5 to about 5 equivalents of concentrated hydrochloric acid in the presence of from about 0.25 to about 4 equivalents of calcium dichloride dihydrate and

TABLE I

Yields and Purities for Chloroalkynes and Alkynyl Amines

| | | | | Chloroalkyne | | Alkynyl Amine | |
|---|---|---|---|---|---|---|---|
| Compound | R | $R^1$ | $R^2$ | % Yield | % Purity | % Yield | % Purity |
| 1 | H | $CH_3$ | $CH_3$ | 85 | 92 | 80 | 85 |
| 2 | H | $C_2H_5$ | $CH_3$ | 92 | 96 | 94 | 95 |
| 3 | H | Cyclohexyl | | 84 | 86 | 90 | 80 | from about 0.001 to about 0.1 equivalent of a copper(I) salt catalyst to produce a chloroalkyne having the formula

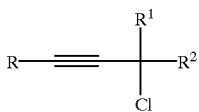

wherein
R is a hydrogen atom, alkyl, cycloalkyl, cycloalkylalkyl or aralkyl and
$R^1$ and $R^2$ are each independently alkyl, cycloalkyl, cycloalkylalkyl, aralkyl or, together with the carbon atom to which they are attached, form cycloalkyl.

2. The process of claim 1 wherein R is a hydrogen atom or lower alkyl, $R^1$ and $R^2$ are each independently lower alkyl or, together with the carbon atom to which they are attached, form cyclopentyl or cyclohexyl, and from about 2 to about 4 equivalents of concentrated hydrochloric acid are employed in the presence of from about 0.5 to about 2 equivalents of calcium dichloride dihydrate and from about 0.005 to about 0.1 equivalent of the copper(I) salt catalyst.

3. The process of claim 2 wherein R is a hydrogen atom, $R^1$ and $R^2$ are each independently methyl or ethyl, the copper catalyst is a copper(I) halide or copper(I) oxide, and from about 0.75 to about 1.5 equivalents of calcium chloride dihydrate and from about 0.01 to about 0.075 equivalent of the copper catalyst are employed.

4. The process of claim 3 wherein $R^1$ is methyl, $R^2$ is methyl or ethyl, and the copper catalyst is copper(I) chloride.

5. The process of claim 4 wherein about 0.05 equivalent of copper(I) chloride is employed.

6. A process for preparing an alkynyl amine that comprises the steps of
(i) preparing a chloroalkyne that consists of reacting an alkynyl alcohol having the formula

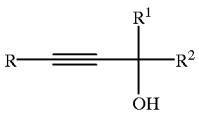

with from about 0.5 to about 5 equivalents of concentrated hydrochloric acid in the presence of from about 0.25 to about 4 equivalents of calcium dichloride dihydrate and from about 0.001 to about 0.1 equivalent of a copper(I) salt catalyst to produce a chloroalkyne having the formula

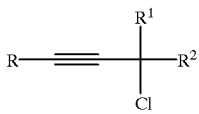

followed by an optional distillation of the chloroalkyne to a purity $\geq 98\%$, and
(ii) reacting the chloroalkyne with from about 1 to about 20 volume equivalents of anhydrous ammonia or an amine having the formula

$HNR^3R^4$ in the presence of from about 1.0 to about 1.5 equivalents of a strong base selected from the group consisting of sodium hydroxide, potassium hydroxide, lithium amide and sodium amide to produce the alkynyl amino having the formula

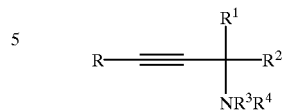

wherein
R is a hydrogen atom, alkyl, cycloalkyl, cycloalkylalkyl or aralkyl,
$R^1$ and $R^2$ are each independently alkyl, cycloalkyl, cycloalkylalkyl, aralkyl or together with the carbon atoms to which they are attached, form cycloalkyl, and
$R^3$ and $R^4$ are each independently a hydrogen atom, lower alkyl or, together with the nitrogen atom to which they are attached, form pyrrolidinyl or piperidinyl.

7. The process of claim 6 wherein R is a hydrogen atom or lower alkyl, $R^1$ and $R^2$ are each independently lower alkyl or, together with the carbon atom to which they are attached, form cyclopentyl or cyclohexyl, and $R^3$ and $R^4$ are each independently a hydrogen atom or lower alkyl; from about 2 to about 4 equivalents of concentrated hydrochloric acid arc employed in the presence of from about 0.5 to about 2 equivalents of calcium dichloride dihydrate and from about 0.005 to about 0.1 equivalent of tho copper(I) salt catalyst are utilized in step (i) followed by distillation of the resulting chloroalkyne to a purity $\geq 98\%$ using a temperature of from about 35° C. to about 140° C. and a pressure of from about 2.6 kPa to about 102 kPa; and in step (ii) from about 1.0 to about 1.25 equivalents of sodium hydroxide, potassium hydroxide or lithium amide are used in the presence of from about 1 to about 10 volume equivalents of anhydrous ammonia or amine.

8. The process of claim 7 wherein R is a hydrogen atom, $R^1$ and $R^2$ are independently methyl or ethyl, $R^3$ and $R^4$ are both hydrogen atoms, and the copper catalyst is a copper(I) halide or copper(I) oxide, from about 0.75 to about 1.5 equivalents of calcium chloride dihydrate and from about 0.01 to about 0.075 equivalent of the copper(I) halide or copper(I) oxide are employed in step (i) followed by distillation of the resulting chloroalkyne to a purity $\geq 98\%$ using a temperature of from about 40° C. to about 80° C. and a pressure of from about 2.6 kPa to about 27 kPa; and in step (ii) about 1.05 equivalents of sodium hydroxide are used in the presence of from about 1 to about 6 volume equivalents of anhydrous ammonia.

9. The process of claim 8 wherein $R^1$ is methyl, $R^2$ is methyl or ethyl, and the copper catalyst is copper(I) chloride.

10. The process of claim 9 wherein about 0.05 equivalent of copper(I) chloride is employed.

11. The process of any of claims 10 further comprising in step (ii) the extraction of the alkynyl amine, after water has been added to dissolve the by-product sodium chloride salt, using an extractant selected from an aliphatic ($C_5$–$C_8$-CR) hydrocarbon, an aromatic hydrocarbon, an aliphatic hydrocarbons substituted with one or more chloro, and chlorobenzene.

12. The process of claim 11 wherein the extractant is a pentane, a hexane, a heptane, benzene, toluene, dichloromethane or chlorobenzene.

13. The process of claim 11 further comprising distilling the alkynyl amine following extraction.

* * * * *